(12) United States Patent
Pomper et al.

(10) Patent No.: US 8,657,354 B2
(45) Date of Patent: Feb. 25, 2014

(54) MOBILE RADIATION THERAPY

(75) Inventors: Mark E. Pomper, Miami Beach, FL (US); Aleksandar Jocic, Wilton Manors, FL (US)

(73) Assignee: Breya, LLC., Miami Beach, FL (US)

( * ) Notice: Subject to any disclaimer, the term of this patent is extended or adjusted under 35 U.S.C. 154(b) by 0 days.

(21) Appl. No.: 13/442,186

(22) Filed: Apr. 9, 2012

(65) Prior Publication Data

US 2012/0207276 A1    Aug. 16, 2012

Related U.S. Application Data

(63) Continuation-in-part of application No. 13/200,803, filed on Sep. 30, 2011, now Pat. No. 8,459,714, which is a continuation-in-part of application No. 13/249,551, filed on Sep. 30, 2011, which is a continuation-in-part of application No. 12/454,109, filed on May 12, 2009, now Pat. No. 8,177,274, which is a continuation of application No. 11/687,225, filed on Mar. 16, 2007, now Pat. No. 7,530,616.

(60) Provisional application No. 60/747,734, filed on May 19, 2006.

(51) Int. Cl.
*A61G 3/00* (2006.01)
*A61N 5/00* (2006.01)

(52) U.S. Cl.
USPC .................. 296/24.38; 296/146.4; 250/493.1

(58) Field of Classification Search
USPC ................ 296/19, 24.3, 24.38, 146.1, 146.4; 250/493.1, 519.1, 515.1, 517.1, 518.1; 976/321
See application file for complete search history.

(56) References Cited

U.S. PATENT DOCUMENTS

| 2,061,419 | A |   | 11/1936 | Ettinger et al. |
|-----------|---|---|---------|-----------------|
| 3,411,002 | A |   | 11/1968 | Armel |
| 3,814,983 | A | * | 6/1974  | Weissfloch et al. ............. 315/39 |
| 3,967,129 | A |   | 6/1976  | Winkler |
| 3,995,165 | A |   | 11/1976 | Buth et al. |
| 4,181,347 | A |   | 1/1980  | Clark |

(Continued)

FOREIGN PATENT DOCUMENTS

| EP | 2061419 | 5/2009 |
|----|---------|--------|
| IL | 195371  | 9/2011 |
| WO | WO 2004/075975 | 9/2004 |
| WO | WO 2007/136733 | 11/2007 |

OTHER PUBLICATIONS

"MinXray", printed from the internet Aug. 13, 2008, but archived by http://web.archive.org on Dec. 23, 2004.

*Primary Examiner* — Jason S Morrow
(74) *Attorney, Agent, or Firm* — Malloy & Malloy, P.L.

(57) ABSTRACT

The invention provides techniques for diagnosing medical conditions and providing appropriate treatment at a patient's home residence. A mobile x-ray team can be dispatched to the patient's home residence. A technical team reviews patient data to determine a proper therapy plan. A mobile radiation therapy apparatus is dispatched to the patient's home as required by the therapy plan. The mobile radiation therapy apparatus includes a radiation source and shielding, and is capable of superficial radiation therapy and/or High Dose Rate (HDR), Low Dose Rate (LDR), and Medium Dose Rate (MDR) implant therapy and/or particle therapy. For HDR, LDR and MDR therapy, the mobile radiation therapy apparatus itself is a specialized radiation vault which the patient will enter. The technical team adjusts the therapy plan based on the additional analysis, and the mobile radiation therapy apparatus is dispatched in accordance with adjusted therapy plan.

18 Claims, 9 Drawing Sheets

(56) References Cited

U.S. PATENT DOCUMENTS

| | | |
|---|---|---|
| 4,449,746 A | 5/1984 | Clark |
| 4,581,538 A | 4/1986 | Lenhart |
| 4,638,166 A | 1/1987 | Baudro |
| 4,754,745 A | 7/1988 | Horowitz |
| 4,833,335 A | 5/1989 | McGinley et al. |
| 5,048,070 A | 9/1991 | Maehama et al. |
| 5,052,036 A | 9/1991 | Grady |
| 5,506,883 A | 4/1996 | Exner |
| 5,727,353 A | 3/1998 | Getz et al. |
| 5,772,574 A | 6/1998 | Nanko |
| 5,859,438 A * | 1/1999 | Nemezawa et al. ........ 250/519.1 |
| 5,908,884 A | 6/1999 | Kawamura et al. |
| 5,929,458 A * | 7/1999 | Nemezawa et al. ........ 250/519.1 |
| 6,017,482 A | 1/2000 | Anders et al. |
| 6,082,799 A | 7/2000 | Marek |
| 6,179,358 B1 | 1/2001 | Hirayama et al. |
| 6,327,338 B1 | 12/2001 | Golovanivsky et al. |
| 6,382,832 B1 | 5/2002 | Schwieker et al. |
| 6,409,651 B1 | 6/2002 | Brown, III |
| 6,445,185 B1 | 9/2002 | Damadian et al. |
| 6,481,887 B1 | 11/2002 | Mirabella |
| 6,604,855 B2 | 8/2003 | Katoh et al. |
| 7,276,716 B1 | 10/2007 | Munro, III |
| 7,442,949 B2 * | 10/2008 | Foster ........................ 250/517.1 |
| 7,530,616 B2 | 5/2009 | Pomper |
| 7,733,089 B2 | 6/2010 | Hobbs et al. |
| 8,016,336 B2 | 9/2011 | Messinger et al. |
| 8,177,274 B2 | 5/2012 | Pomper |
| 2002/0154742 A1 | 10/2002 | Feldman |
| 2003/0102463 A1 | 6/2003 | Smith |
| 2003/0176779 A1 | 9/2003 | Ghelmansarai |
| 2003/0179854 A1 | 9/2003 | Jaafar |
| 2004/0075975 A1 | 4/2004 | Song |
| 2004/0165696 A1 | 8/2004 | Lee |
| 2004/0217307 A1 * | 11/2004 | Bruchle et al. .............. 250/518.1 |
| 2005/0099145 A1 * | 5/2005 | Nishiuchi et al. ............. 315/500 |
| 2007/0136733 A1 | 6/2007 | Park et al. |
| 2007/0164238 A1 | 7/2007 | Pomper |
| 2007/0269008 A1 | 11/2007 | Pomper |
| 2008/0036232 A1 | 2/2008 | Randjelovi et al. |
| 2008/0317202 A1 * | 12/2008 | Partain et al. ................... 378/37 |
| 2009/0110152 A1 | 4/2009 | Manzke et al. |
| 2009/0175414 A1 | 7/2009 | Messinger et al. |
| 2009/0252293 A1 | 10/2009 | Pomper |
| 2009/0268870 A1 | 10/2009 | Pomper |
| 2010/0102244 A1 * | 4/2010 | Zdasiuk et al. ........ 250/396 ML |
| 2011/0213192 A1 | 9/2011 | Levy et al. |
| 2012/0069961 A1 | 3/2012 | Pomper et al. |
| 2012/0112092 A1 | 5/2012 | Pomper et al. |

* cited by examiner

MOBILE RADIATION THERAPY

CLAIM OF PRIORITY

The present application is a continuation-in-part application of application having Ser. No. 13/200,803, filed on Sep. 30, 2011 now U.S. Pat. No. 8,459,714 which is a continuation-in-part application of pending application having Ser. No. 13/249,551, filed on Sep. 30, 2011 which is a continuation-in-part application of application having Ser. No. 12/454,109, filed on May 12, 2009 now U.S. Pat. No. 8,177,274, which is a continuation application of application having Ser. No. 11/687,225, filed on Mar. 16, 2007, which matured into U.S. Pat. No. 7,530,616 on May 12, 2009, which claims priority to U.S. Provisional Application No. 60/747,734, filed on May 19, 2006, which are incorporated herein by reference in their entirety.

BACKGROUND OF THE INVENTION

Field of the Invention

Radiation Therapy is one of the three primary methods to treat cancer; the others include surgery and chemotherapy. Radiation treatment typically requires multiple sessions (often over 20), and therefore may require a great deal of travel time wherein the patients must come into a cancer center for treatment. Additionally, patients are often required to endure prolonged time periods in waiting rooms at the cancer center for their treatments, even though these actual treatments are generally quick. This extensive queuing is most difficult for patients who are sick and infirm, which comprises a significant percentage of cancer patients.

Previous attempts to provide mobile radiation therapy are founded in the notion of merely creating satellite stationary treatment centers. For example, a radiation therapy center such as described in U.S. Pat. No. 4,449,746 can be set up in one location for an entire day, and then relocated to another location for the next day. Although this approach does create increased access to care, it fails to address the special needs of very sick and feeble patients because these patients must find the means to travel to the satellite center. The consequences of missing radiation therapy sessions or consultation visits can be life threatening.

SUMMARY OF THE INVENTION

The invention provides patients with a quality of radiation therapy, which is substantially similar to current fixed location cancer centers, but without the need to travel to the center. The mobile aspects of the invention provide a quality treatment experience, because fewer appointments are missed and a higher percentage of completed therapy protocols are accomplished. Additionally, a commonly seen phenomena of patient procrastination (i.e. wherein patients do not come to their initial consults, or even make their appointments) is reduced. The invention assists in the treatment of patients who are currently unable (or are able only with major difficulties) to obtain radiation therapy.

In one aspect, the invention provides a mobile radiation treatment apparatus including a radiation source configured to emit radiation, a patient treatment table disposed in proximity to the radiation source, an operator control station, an operator shield assembly disposed between the operator control station and the radiation source, the operator shield assembly configured to reduce exposure to a user located at the operator control station from the radiation emitted from the radiation source, and a plurality of shielding sections configured to enclose the radiation source, the patient treatment table, the operator control station, and the operator shield assembly in a compartment, such that the compartment is at most approximately 20 to 30 feet in length, 7 to 12 feet in width, and 6 to 8 feet in height, and the plurality of shielding sections are disposed to substantially impede the radiation emitted from the radiation source.

Implementations of the invention may include one or more of the following features. The mobile radiation treatment apparatus includes two patient area radiation bulkheads disposed to enclose the patient treatment table, such that each patient treatment table radiation bulkhead includes a door configured to allow access to the patient treatment table. The patient treatment table is optionally configured to be selectively raised and lowered. The mobile radiation treatment apparatus includes a patient table shield disposed around the patient treatment table, and is configured to impede the radiation emitted from the radiation source, thereby reducing the amount of radiation or eliminating emission of radiation outside of the treatment area. For example, the amount of radiation is reduced by 10, 25, 50, 75, 100% compared to the amount detected in the treatment area. The patient treatment table is configured to be selectively raised to a height above the patient table shield, and selectively lowered to a height at the bottom of the patient table shield. The radiation source can be moved from a first position to a second position when the patient treatment table is lowered into the patient table shield. The volume of the compartment in the mobile radiation treatment apparatus is less than 2,200 cubic feet. For example, a mobile radiation treatment apparatus can be 850 cubic feet, or 1500 cubic feet. The compartment is configured to attach to a flatbed vehicle.

In another aspect, the invention provides a mobile radiation therapy apparatus including a vehicle cabin with driving controls for operating the vehicle, a patient treatment compartment coupled to the vehicle cabin, a radiation source configured to emit radiation, and disposed within the patient treatment compartment, a patient treatment table disposed within the patient treatment compartment and in proximity to the radiation source, a treatment table radiation shield disposed around the patient treatment table, and configured to impede the radiation emitted from the radiation source, and a plurality of radiation shield sections rigidly attached to the patient treatment compartment, and configured to substantially impede the radiation emitted from the radiation source.

Looking to further embodiments of the present invention, the mobile radiation treatment apparatus preferably includes at least two patient area radiation bulkheads configured to define a compartment, and at least one non planar door moveably connected to at least one of the bulkheads. The non-planar door is configured to enclose the compartment and define an interior of the compartment that extends beyond an edge of at least one of the radiation bulkheads. In that manner, a larger interior of the compartment can be defined. It is at least partially within this interior of the compartment that the radiation source is disposed. Conversely, outside of the compartment, and in spaced relation from the radiation source, is an operator control station operably connected to the radiation source and configured to control the radiation emitted by the radiation source.

Further, such a mobile radiation treatment apparatus can be disposed in or on a cabin that is associated with a vehicle. The shielded radiation sources are disposed in the cabin in a manner which, along with the at least one non-planar door, encloses the radiation source within the compartment, thereby ensuring minimal if any exposure to the radiation emitted by the radiation source outside of the container. Nevertheless, so as to further increase the safety to the operator, it may be preferred that the cabin be of a sufficiently elongate configuration to allow for sufficient spacing for the operator control station. In one preferred embodiment the operator control station is at least 10 feet from the enclosed compartment.

Implementations of the invention may include one or more of the following features. The mobile radiation therapy apparatus includes a radiation source that is configured to emit radiation for high-dose radiation (HDR) therapy (i.e. 500-2000 centigray/hr at 1 centimeter at energy ranges into the KeV and/or MeV range).

The radiation source is configured to emit radiation to support variable low dose rate therapy (i.e. less than 500 cGy/hr at 1 cm). The radiation source is configured to emit radiation to support dose rates that are greater than 2000 centigray/hr at 1 centimeter. The radiation source is configured to emit radiation in short pulses. The proper dose ranges would be understood by those skilled in the art based on the treatment regimen and the disorder or illness being treated.

Also, implementations of the invention may include one or more of the following features. The mobile radiation therapy apparatus includes a control tether for connecting the patient treatment compartment to the radiation source, such that the radiation source is relocated outside of the patient treatment compartment, portable radiation shields configured to be removed from the patient treatment compartment and disposed in proximity to the radiation source, and a control computer operably connected to the radiation source and configured to control the radiation emitted by the radiation source.

Also, implementations of the invention may include a wireless connection to the internet, and an x-ray imaging system. The mobile radiation therapy apparatus may further include a chemotherapy treatment device, such that the patient treatment compartment is utilized to provide chemotherapy to a patient.

The invention also provides a method for providing mobile radiation therapy including conducting a house call with a patient, dispatching a mobile x-ray team to a treatment location (e.g., patient's residence, local physician's office), performing a technical review of patient data, creating a mobile radiation therapy plan, dispatching a mobile radiation therapy apparatus to the treatment location, and administering radiation therapy in accordance with the mobile radiation therapy plan.

Implementations of the invention may include one or more of the following features: dispatching the mobile x-ray team on a periodic basis as part of the mobile radiation plan; administering radiation therapy including high-dose radiation therapy; administering radiation therapy including variable low-dose radiation therapy; administering radiation therapy including medium-dose radiation therapy; administering radiation therapy including particle therapy and performing the technical review of patient data which is completed after each administering of radiation therapy.

In accordance with implementations of the invention, one or more of the following capabilities may be provided. Increased radiation shielding in and around a patient table reduces the requirements for shielding around a larger patient compartment. Patient treatment table shielding, patient area radiation bulkheads, shielding panels, operator shield assemblies and/or compartment shielding may be comprised of glass panels and/or installed in a motorized vehicle. Furthermore, the glass panels may comprise leaded glass. Radiation therapy can be provided away from a hospital environment. High, medium and low dose radiation therapy and particle therapy can be provided at a patient's home residence, or a local physician's place of practice. Radiation therapy can be administered in a detached mode. Mobile radiation therapy can be incorporated into a radiation therapy plan.

In another embodiment, the patient treatment table shielding, patient area radiation bulkheads, shielding panels, operator shield assemblies and/or compartment shielding may be comprised of panels, such as glass or acrylic panels, that are adapted to form one or more substantially enclosed liquid fillable interior spaces such that the space may be filled with a liquid, such as water, to further impede radiation leakage to surrounding areas.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Embodiments of the invention provide techniques for diagnosing and evaluating medical conditions and providing appropriate treatment at a patient's home residence. A physician, or other qualified personnel, conducts an initial house call with a patient to gather personal and medical data. A mobile x-ray diagnostic team may be subsequently dispatched to the patient's home residence. A technical team reviews patient data to determine the proper therapy plan. Additional house visits and/or telephone interviews may be conducted. A mobile radiation therapy apparatus is dispatched to the patient's home as required by the therapy plan. The mobile radiation therapy apparatus (MRTA) includes a radiation source and shielding, and is capable of superficial radiation therapy, particle therapy (e.g., proton, neutron and heavy ion therapies), and/or High Dose Rate (HDR), Medium Dose Rate (MDR), and Low Dose Rate (LDR) implant therapy. The MRTA is used to deliver 1 MeV of radiation. In other embodiments, the MRTA is used to deliver less than 1 MeV of radiation. In yet other embodiments, the MRTA is used to deliver greater than 1 MeV of radiation. For HDR therapy, the mobile radiation therapy apparatus itself is a specialized radiation vault which the patient will enter. Therapy data is stored in the mobile radiation therapy apparatus and transferred to the technical team for additional analysis. The technical team adjusts the therapy plan based on the additional analysis, and the mobile radiation therapy apparatus is dispatched in accordance with adjusted therapy plan.

Figure 1:
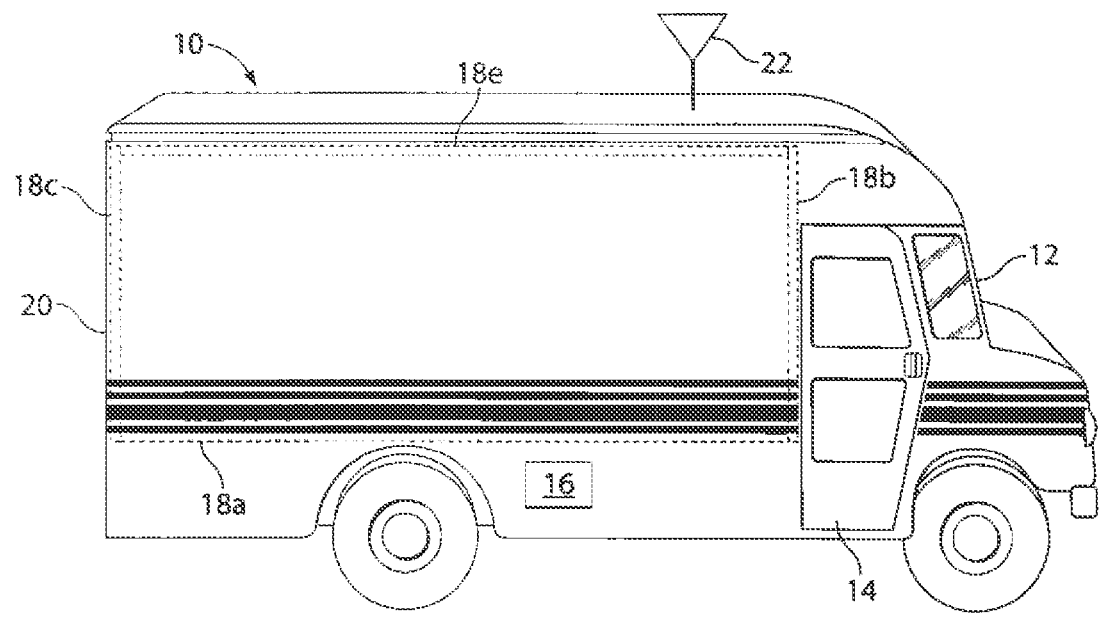
FIG. 1 is a profile side view of a mobile radiation therapy apparatus.

Referring to FIG. 1, a mobile radiation therapy apparatus (MRTA) 10 comprises a vehicle cabin 12, at least one patient access door 14, an interface panel 16, radiation shielding sections 18a, 18b, 18c, 18e, a patient treatment compartment 20, and in at least one embodiment, at least one wireless communication antenna 22. The MRTA 10, including the vehicle cabin 12 and the patient treatment compartment 20, is sufficiently compact in size to travel within an urban population center to a patient's parking lot or driveway (e.g. the patient treatment compartment is approximately 20' to 30' in length by 7' to 12' in width). The vehicle cabin 12 includes the driving controls for the MRTA 10 and may be detachable from the patient treatment compartment 20. For example, the MRTA 10 may be designed as a pod which is capable of being carried on a flatbed vehicle. In one embodiment, the MRTA 10 is designed as a trailer which is capable of being coupled and uncoupled from a vehicle. Further, the MRTA 10 is capable of being air-lifted into an area, and operates independent of the vehicle (e.g., to provide radiation therapy when roads have become inaccessible). Further, the MRTA 10 may be designed as a portable enclosure, with a patient treatment compartment defined within, with the enclosure structured to be at least temporarily secured to a vehicle and to move with the vehicle.

In one embodiment, such as for use in urban areas where street and parking space is generally less available, the MRTA 10 includes a combination vehicle cabin 12 and patient treatment compartment 20 that are rigidly connected (e.g., a standard delivery truck such as the Freightliner M2-106). This rigid connection decreases the overall footprint of the MRTA 10.

The patient treatment compartment 20 includes at least one patient access door 14 to permit access to and egress from the interior of the patient treatment compartment 20. The patient access door 14 may include ramps or other lifting devices to improve access for non-ambulatory patients. The patient treatment compartment 20 includes a plurality of radiation shielding sections 18a-e (e.g. lead, aluminum, alloys of lead, titanium, water, polymers (such as plastic), acrylic, glass, leaded glass, concrete and fiberglass). The position and number of radiation shield sections 18a-e are exemplary only and not a limitation as additional sections of radiation shielding may be included to meet existing shielding requirements (e.g., federal and state regulations, ALARA recommendations). Also, the thickness and location of the radiation shielding sections 18a-e is dependent on the type of shielding material used, and the configuration of the interior of the patient treatment compartment 20 (e.g. the location of the radiation source, the treatment table, and interior radiation shields). For example, the shielding material may be lead with a thickness between 0.25" and 2.0" based on location within the MRTA 10.

Furthermore, embodiments of the present invention may include the plurality of radiation shielding sections comprised of wall panels, such as glass or acrylic panels, each of the wall panels including a liquid fillable interior space structured to receive a radiation impeding liquid therein when radiation is to be emitted from the radiation source and to be emptied of liquid when the portable enclosure is to move with the vehicle, thereby reducing the weight to be moved by the vehicle.

The whole of the MRTA 10 is considered as a radiation vault with shielding affixed and disposed on the outer boundary of the MRTA 10, where practical (e.g., on the body of the MRTA vehicle, and on a divider behind the driver compartment, 18b). For example, as shown in FIG. 1, a MRTA 10 includes dimensions of approximately 20 to 30 feet in length, by 7 to 12 feet in width, with an inner height of 6 to 8 feet. With a radiation source located in the center of the MRTA 10, and directed towards a shielded treatment table, the thickness of the radiation shielding sections at the front and rear of the MRTA 10 (i.e., sections 18b,c) is approximately 1.37 inches of lead. The thickness of the radiation shielding on the sides of the MRTA 10 (i.e., sections 18a, and 18d (see FIG. 4)) is approximately 0.88 inches of lead. The thickness of the radiation shielding on the ceiling of the MRTA 10 (i.e., section 18e) is approximately 1.18 inches of lead. These values are exemplary only as the number, geometry and thickness of the sections will be modified based on the radiation source configuration as well as patient table shielding, and optional interior shielding, if any.

The MRTA 10 is capable of generating and receiving power and communication signals. The interface panel 16 includes connection ports for power and communication systems. For example, the patient treatment compartment 20 is capable of receiving power (e.g. 120 v, 60 Hz) and communication inputs (e.g. cable television signals, Internet access) from external sources. The interface panel 16 is also capable of providing power from generators and batteries installed within the MRTA 10, and communication signals from onboard computer systems, in support of detached operations. The wireless antenna 22 is a component of an onboard computer system and provides access to the Internet via commercial broadband signals (e.g. Verizon BroadbandAccess™). The wireless antenna 22 also supports a wireless local area network (e.g. Wi-Fi, Bluetooth, WiMAX, HomeRF) to support detached operations.

Figure 2:
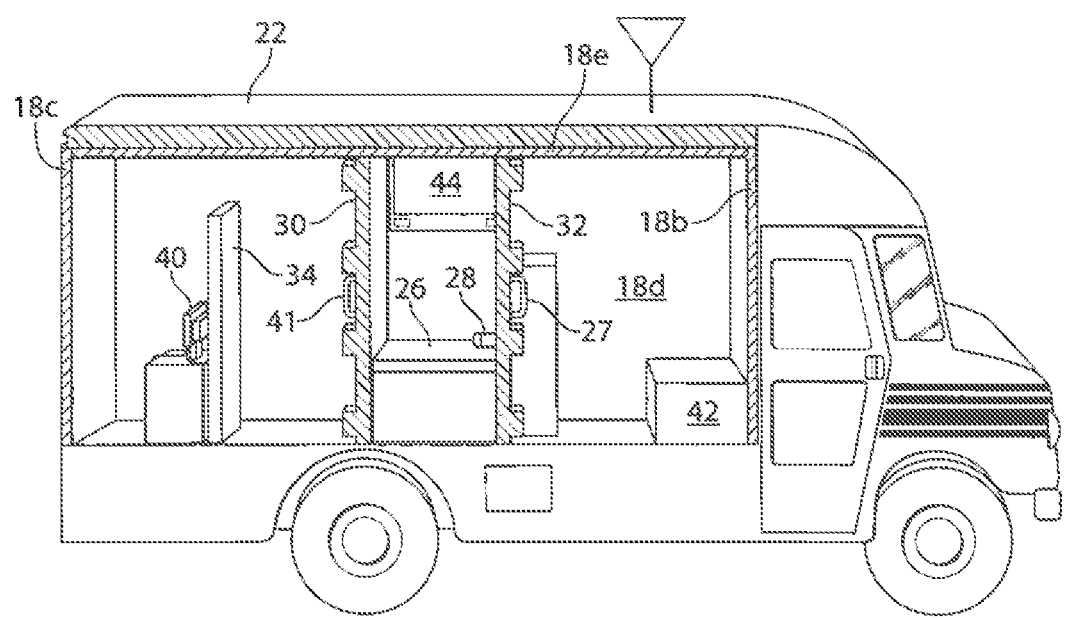
FIG. 2 a partial interior view of a mobile radiation therapy apparatus.

Regarding FIG. 2, the patient treatment compartment 20 includes a treatment table 26, a radiation source 28, optional patient area radiation bulkheads 30, 32 with access doors 27, 41, and operator radiation shielding 34 (or operator shield assembly), an operator control station 40, a control power system 42, and a patient entertainment device 44. In general, the patient treatment compartment 20 is configured to include an interior that is conducive to patient relaxation (e.g., soft lighting, frosted glass partitions etched with scenes of local beauty, and a sound system for appropriate music). In one embodiment, the treatment table 26 is enclosed within optional patient area radiation bulkheads 30, 32. In some embodiments, the construction of the treatment table 26 includes radiation shielding material that is configured to impede radiation emitted from a high energy source (i.e. greater than 250 kV of radiation). In general, the radiation shielding (including wall panels) used within the MRTA 10 includes, but is not limited to, lead, aluminum, alloys of lead, titanium, water, polymers (such as plastic), acrylic, concrete, glass, leaded glass, and fiberglass. When acrylic, water, polymers, fiberglass and/or glass are utilized, they may be at least partially transparent so as to permit light to enter the patient treatment compartment 20. The treatment table 26 is disposed to impede the radiation emitted from the radiation source 28 from passing through the bottom of the MRTA 10. The optional patient area radiation bulkheads 30, 32, and the material within the treatment table 26, are of sufficient density to provide at least a partial barrier during High Dose Rate (HDR) implant therapy. For example, the upper portion of the optional patient area radiation bulkheads 30, 32 (i.e. the portion above the treatment table 26) is comprised of 0.46 inches of lead. The lower portions of the radiation bulkheads 30 and 32 can be comprised of less radiation shielding due to the location of the shielding in the treatment table 26 in relation to the radiation source 28.

Furthermore, patient area radiation bulkheads, operator shield assemblies, and/or treatment table radiation shields may be comprised of a plurality of panels (or wall panels), such as glass (possibly leaded glass), plastic, or acrylic panels, that are adapted to form the structure. The panels include one or more substantially enclosed liquid fillable interior spaces between the panels, such that the space may be filled with a liquid, such as water, to further impede radiation leakage into surrounding areas. The plurality of panels may be further configured to provide at least one opening structured to facilitate the introduction and removal of liquid relative to the liquid fillable interior space. Such a configuration decreases the weight of the MRTA 10 during transit and allows for the panels to be filled with liquid once the MRTA reaches a destination and is ready for use.

In some embodiments, the MRTA 10 may comprise at least one movable radiation bulkhead structured to open and close so as to provide access into and out of an interior of the patient treatment compartment and to at least partially enclose the radiation source when in a closed orientation. The moveable radiation bulkhead may be comprised of a wall panel, the wall panel including a liquid fillable interior space structured to receive a radiation impeding liquid therein when radiation is to be emitted from the radiation source and to be selectively emptied of liquid when the radiation source is not in use. This configuration also allows for reducing the weight of the moveable bulkhead during opening and closing and during movement of the vehicle.

In some embodiments, the treatment table 26 does not contain radiation shielding materials. In such embodiments, the lower portions of the radiation bulkheads 30 and 32 and/or radiation shield sections 18*a-e* may be comprised of additional radiation shielding if necessary to prevent radiation from passing through the MRTA 10.

In one embodiment, the height of the patient table 26 is adjustable and the radiation bulkheads 30, 32 are of a more uniform thickness from top to bottom. The patient table 26 can be raised, lowered and tilted to improve the alignment between the radiation source 28 and the patient. Also, the position of the patient table 26 can be adjusted to assist in transferring wheelchair bound patients onto and off of the table 26.

The access doors 27, 41 are composed of radiation shielding material and are configured to allow patients and medical personnel to enter the patient treatment compartment 20 and access the treatment table 26. The doors 27, 41 include, or are capable of integrating with, patient transfer systems to assist in moving a patient from a stretcher, wheelchair, or seat, to the treatment table 26. The patient treatment compartment 20 may also include lift wheelchairs and stretchers. Further, the treatment table 26 is configured to rotate the patient to an appropriate position for therapy.

The radiation source 28 is configured to provide a dosage appropriate for a prescribed therapy plan. In general, as an example and not a limitation, the radiation source 28 includes a 192Ir source. Other radiation sources may be used for other radiation based treatments (e.g. gamma knife treatment generated from Cobalt-60). For example, if the therapy plan requires a variable low dose rate, then the MRTA 10 will be configured to include a Nucletron microSelect PDR™ as the radiation source 28. In another example, if the therapy plan requires a high dose rate, then the MRTA 10 will be configured to include a Nucletron microSelect HDR™ as the radiation source 28. The invention is not limited to the selection of a single Nucletron source, nor is it limited to a single supplier of radiation sources. In another example, the Xoft Axxent™ HDR X-ray Source 2.2 and associated Axxent™ controller will be used.

In another example, the radiation source 28 may be a source useful for particle therapy (e.g., proton, neutron and heavy ion therapies). For example, the radiation source 28 may include a linear particle accelerator, providing an electron, proton, or heavy ion source (e.g., CYBERKNIFE®)).

Further, in addition to the radiation source 28, the MRTA 10 is configured with an optional portable X-ray imaging device, such as MinXray HF100H system.

Generally, photons (X-rays) are used for treating tumors deep within the body. Electrons, which cannot penetrate deep tissue, are used for more superficial disease including some skin cancers and shallow head and neck lesions. High dose radiation is used to treat tissues deep within the body (e.g., 5 cm, 10 cm, 15 cm, 25 cm, or more from the body surface). Specialized catheters and applicators are used to deliver radiation to a specific area of the body (e.g. remote sites and difficult to access anatomical areas). That is, HDR methods are used to administer radiation to internal sites to kill or inhibit the proliferation of tumors within the body. For example, the methods are useful to treat tumors associated with internal organs such as liver, kidney, lung as well as other tissues or lumens within the body. For example, patients to be treated include those that have been diagnosed with a cell proliferative disorder such as breast cancer, prostate cancer, brain cancer, Hodgkin's Lymphoma, Non-Hodgkin's Lymphoma, bladder cancer, leukemia, cancer of the colon/rectum, uterine cancer, ovarian cancer, and cancer of the eye. In general, the higher dose rates and energy ranges associated with HDR methods provide benefits such as reduced treatments times and improved patient comfort.

The disposition of the radiation source 28 in FIG. 2 is exemplary only and not a limitation as alternative mounting configurations are also envisioned. For example, the radiation source 28 may be mounted on the ceiling of the MRTA 10 and be disposed to deliver radiation to a patient below the radiation source 28. Further, multiple sources may be installed in a single MRTA 10 such as from both a side and an overhead mount. Portable radiation sources are also included in the MRTA 10 as bulkhead spares, to be configured prior to a radiation therapy session. Combinations of sources rigidly fixed within the MRTA 10, and portable sources which are stored within the MRTA 10 are envisioned. The patient treatment compartment 20 may include an additional door configured to facilitate the installation and removal of the portable radiation sources. Further, portable sources will be configured to connect to the interface panel 16 during detached operations.

The operator control station 40 is disposed behind radiation shielding 34 and is operatively connected to the MRTA 10. For example, the radiation shielding 34 is approximately 1 inch thick lead, and is disposed to shield an operator working at the control station 40. In one embodiment, the radiation shielding 34 is divided into 2 sections such that the upper section is comprised of 1 inch thick lead, and the lower section is comprised of 0.53 inch thick lead. The reduction in lead for the lower half of the shielding 34 is based on the influence of the optional patient area bulkhead 30 and the patient table 26. Alternatively, glass may be used instead of lead; particularly useful is leaded glass. In one embodiment, the operator control station 40 is located outside of the patient treatment compartment 20 (i.e. under a canopy outside of the vehicle). In yet another embodiment, the radiation shielding may be comprised of a plurality of panels, such as glass (possibly leaded glass), plastic, or acrylic panels, that are adapted to form the structure of the radiation shielding and to form one or more substantially enclosed liquid fillable interior spaces between the panels such that the space may be filled with a liquid, such as water, to further impede radiation leakage into surrounding areas. The plurality of panels may be further configured to provide an inlet and outlet, whereby liquid may enter and exit the radiation bulkhead.

The operator control station 40 comprises networked computer processors, the computer processors including input and output devices, configured to control the MRTA 10 subsystems (e.g. doors and interlocks, patient table height and orientation, climate control, power generation, Internet connectivity) as well as control the radiation source 28, and store patient therapy data. The operator control station 40 also includes data processing capabilities to manipulate and display the stored patient data, and is capable of sending and receiving information via the internet through the wireless antenna 22. The power control system 42 includes power generation and control equipment capable of providing electrical power to the MRTA 10, including the radiation source 22 and operator control station 40. In one embodiment, the power control system 42 receives electrical power through the interface panel 16 thus reducing the need to generate power within the MRTA 10.

The patient entertainment device 44 is disposed within sight of the patient table 26 and is configured to provide multimedia content to the patient during therapy.

Figure 3:
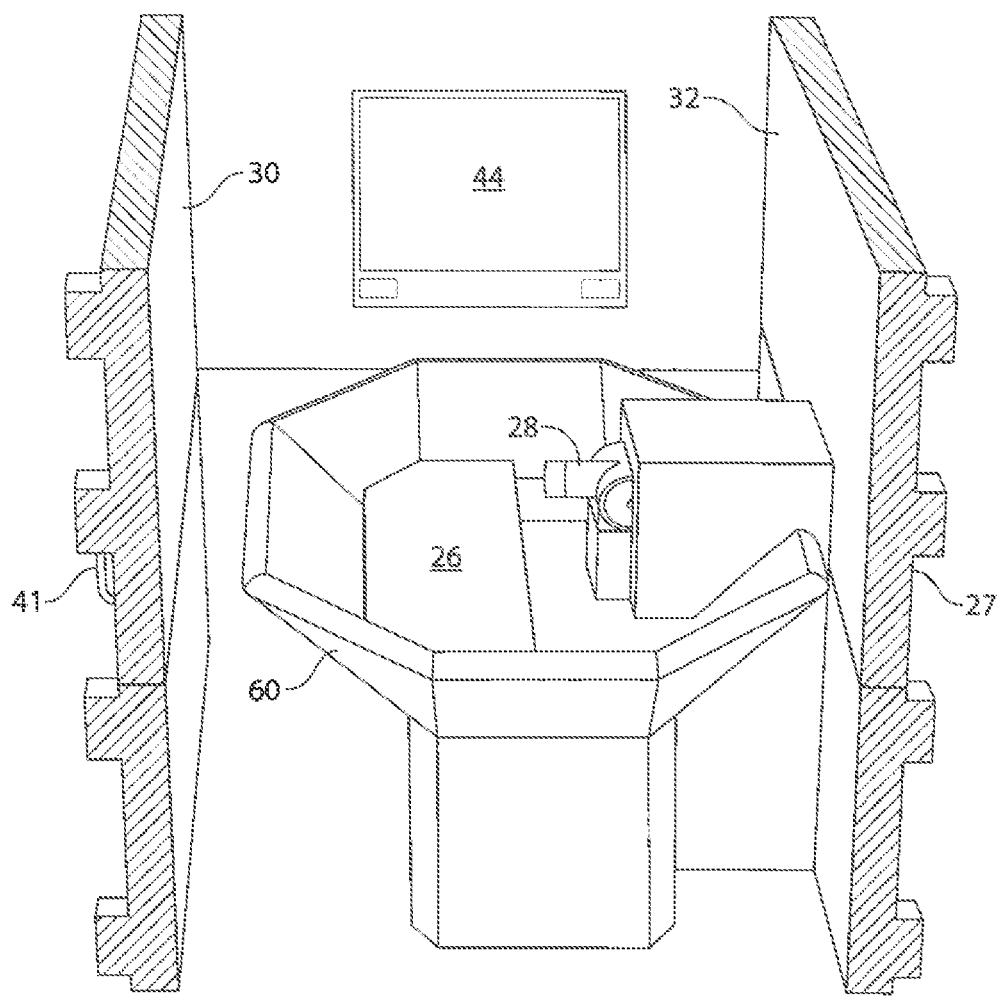
FIG. 3 a view of a patient table shield with optional patient bulkhead shielding.

Regarding FIG. 3, with further reference to FIG. 2, the patient treatment compartment 20 in the MRTA 10 includes the treatment table 26, the radiation source 28, optional patient area radiation bulkheads 30, 32 with access doors 27, 41, a patient entertainment device 44, and a patient table shield 60. The patient table shield 60 is configured around the patient table 26 and disposed to reduce the amount radiation energy entering the patient treatment compartment 20. The height and configuration of the patient table shield 60 is exemplary only, as the location and type of radiation source will impact the necessary geometry of the radiation shielding. In at least one embodiment, the patient table 26 can be lowered into, or is disposed within, a patient table shield 60 that is configured as a vertical wall around the circumference of the patient table 26; the height of the vertical wall is in a range between 6 to 18 inches. As known in the art, installation adjustments of the radiation shielding (e.g., 18a-e, 26, 30, 32, 34, and 60) will be required to reduce radiation hot spots within and beyond the MRTA 10.

Figure 4:
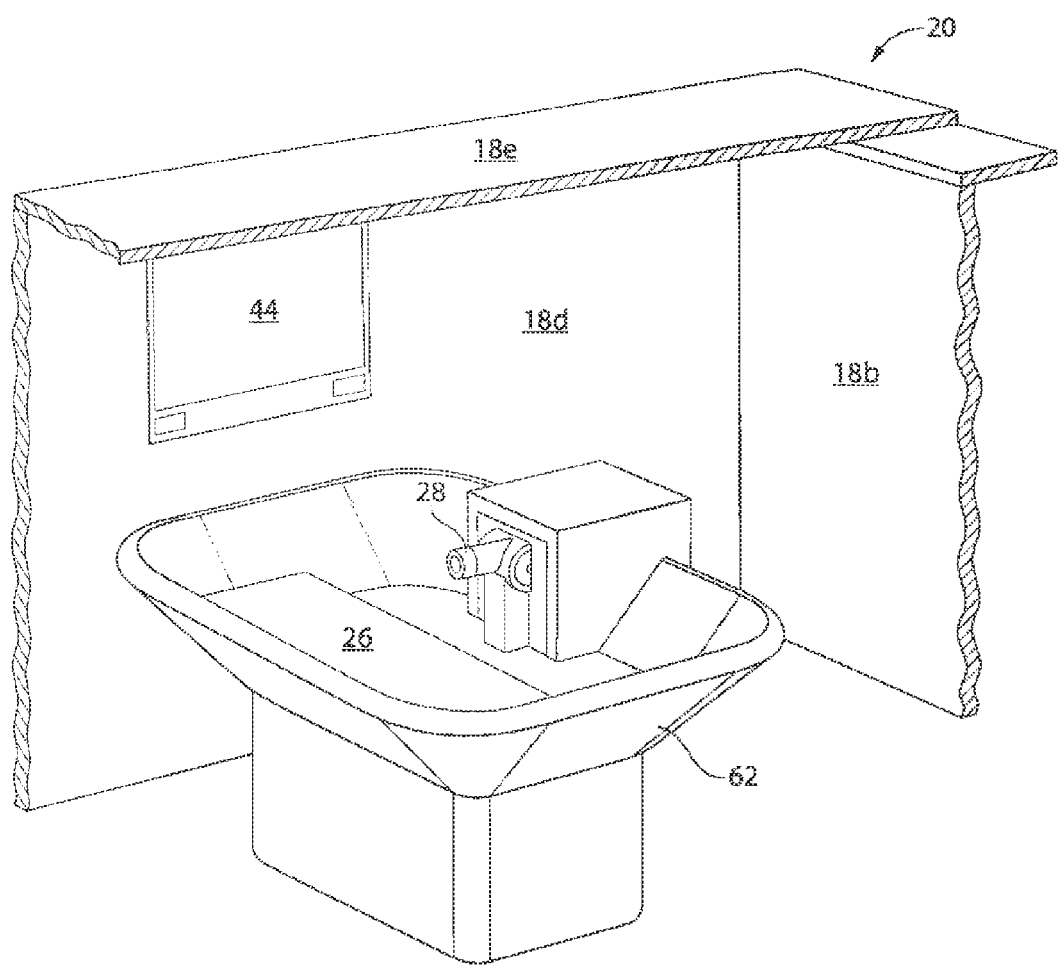
FIG. 4 a view of a patient table shield without bulkhead shielding.

Referring to FIG. 4, with further reference to FIGS. 1-3, the patient treatment compartment 20 includes a treatment table 26, the radiation source 28, the patient entertainment device 44, and a patient table shield 62. The patient treatment compartment 20 is enclosed by radiation shield sections 18a-e (n.b., radiation shield sections 18a,c are not shown in FIG. 4 because of the perspective of the illustration). The radiation source 28, treatment table 26, and patient table shield 62 are installed against one of the radiation shields 18b. The height and angle of the patient table shield 62 are exemplary, and not a limitation as the configuration will change based on the relative location of the radiation source 28. In one embodiment, portions of the patient table shield 62 are on hinges and configured to fold down to provide direct access to the treatment table 26. The hinged portion of the patient table shield 62 is further configured to lock in the upright position after a patient is placed on the treatment table 26.

Figure 5:
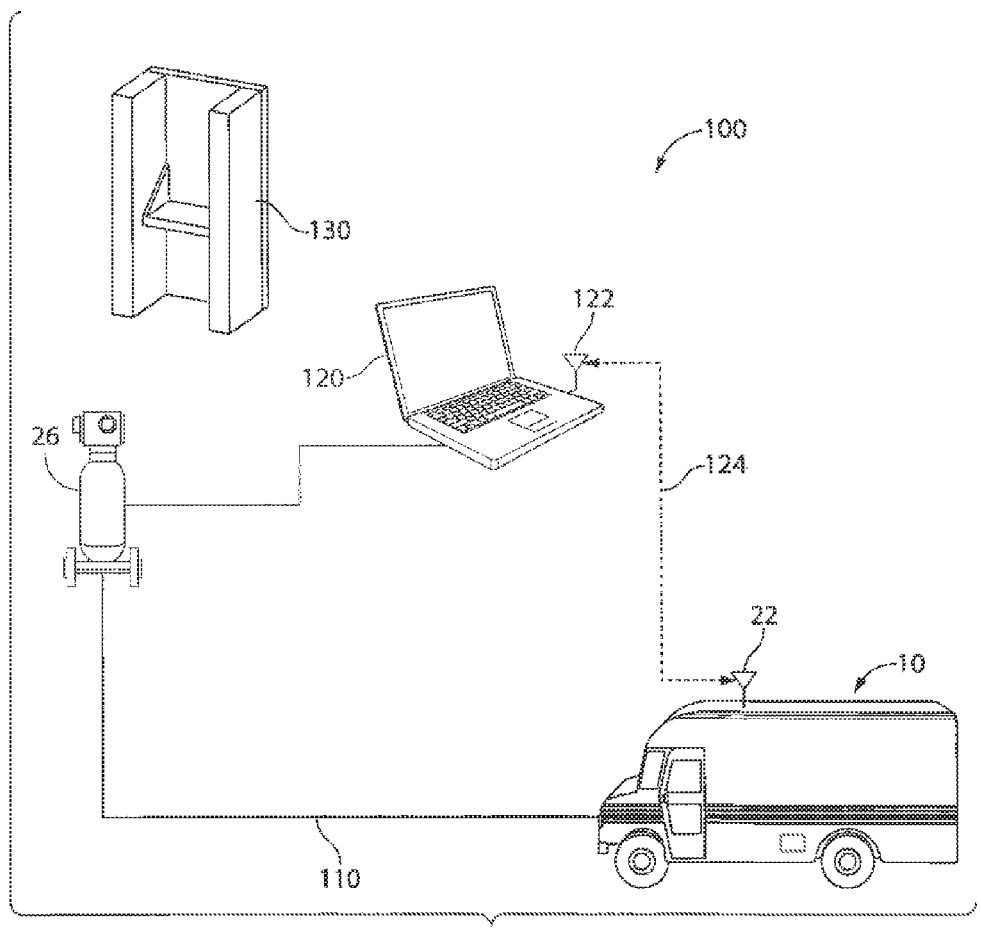
FIG. 5 a system diagram of detached radiation therapy configuration.

Referring to FIG. 5, with further reference to FIG. 1, a system diagram of detached radiation therapy 100 is shown. Detached operation includes the MRTA 10, the communication antenna 22, the radiation source 28, a control tether 110, a local computer 120, a wireless network interface 122, a wireless data connection 124, and portable shielding 130. The MRTA 10 is configured to connect to the control tether 110 through the interface port 16. The control tether 110 includes power and data communication portions, and is configured to connect to the radiation source 28. The local computer 120 connects to the radiation source 28 and is configured with corresponding control software for monitoring and controlling the radiation source 28. The local computer 120 is also configured to communicate with the MRTA 10 through the control tether 110, or via wireless network interface 122, and the wireless data connection 124. The portable shielding 130 is configured to be removed from the MRTA 10 and moved into a residential space (e.g., through standard doors and stairwells). The portable shielding 130 can be comprised of multiple blocks of a shielding material (e.g. lead, aluminum, alloys of lead, Ledite®, titanium, polymers (such as plastic), acrylic, concrete, glass, leaded glass, and fiberglass) which are assembled in the detached location. The portable shielding 130 may also be shaped plastic, acrylic, or glass containers that are assembled and filled with water in the detached location. For example, the portable shielding can be flexible bladders disposed within a frame assembly and configured to be filled from a hose connected to an examining room sink. These embodiments of the portable shielding are exemplary and not limiting as other configurations of portable shielding are envisioned.

In operation, the elements within the MRTA 10 such as the radiation source 28, computer control system 40, and bulkheads 30, 32 can be detached from the MRTA 10 and set-up in the patient's home. In detached operation 100, the elements of the MRTA are tethered to the MRTA 10 via a control tether 110, including cables for power and data communications. The data communication between the local computer 120 and the MRTA 10 is established via wireless link 122, 124, 22. Communications may also be established via cables (i.e. Ethernet connections) within the control tether 110. The computer control system 40 is capable of bridging the wireless link 122, 124, 22, and cable connections, to the internet. In one embodiment, power to the radiation source 28 is provided locally from the patient's residential service.

The detached operation 100 is not limited to a patient's residence. The MRTA 10 can also be dispatched to a physician's office. Such an office may include a pre-installed or quasi-permanent radiation shielding apparatus. A practicing physician may desire to provide radiation therapy within their office without making the substantial investment in the corresponding equipment and personnel. Accordingly, detached operation 100 provides local physicians the ability to supervise and monitor the radiation therapy provided to their patients. The MRTA 10 can be configured to transmit and receive patient data to and from the local physician's database system through a LAN or the Internet. Further, other hardware components of the MRTA 10 (i.e. the patient treatment table 26, the operator station 40) can be removed from the MRTA 10 and disposed within the local physician's office.

Figure 6:
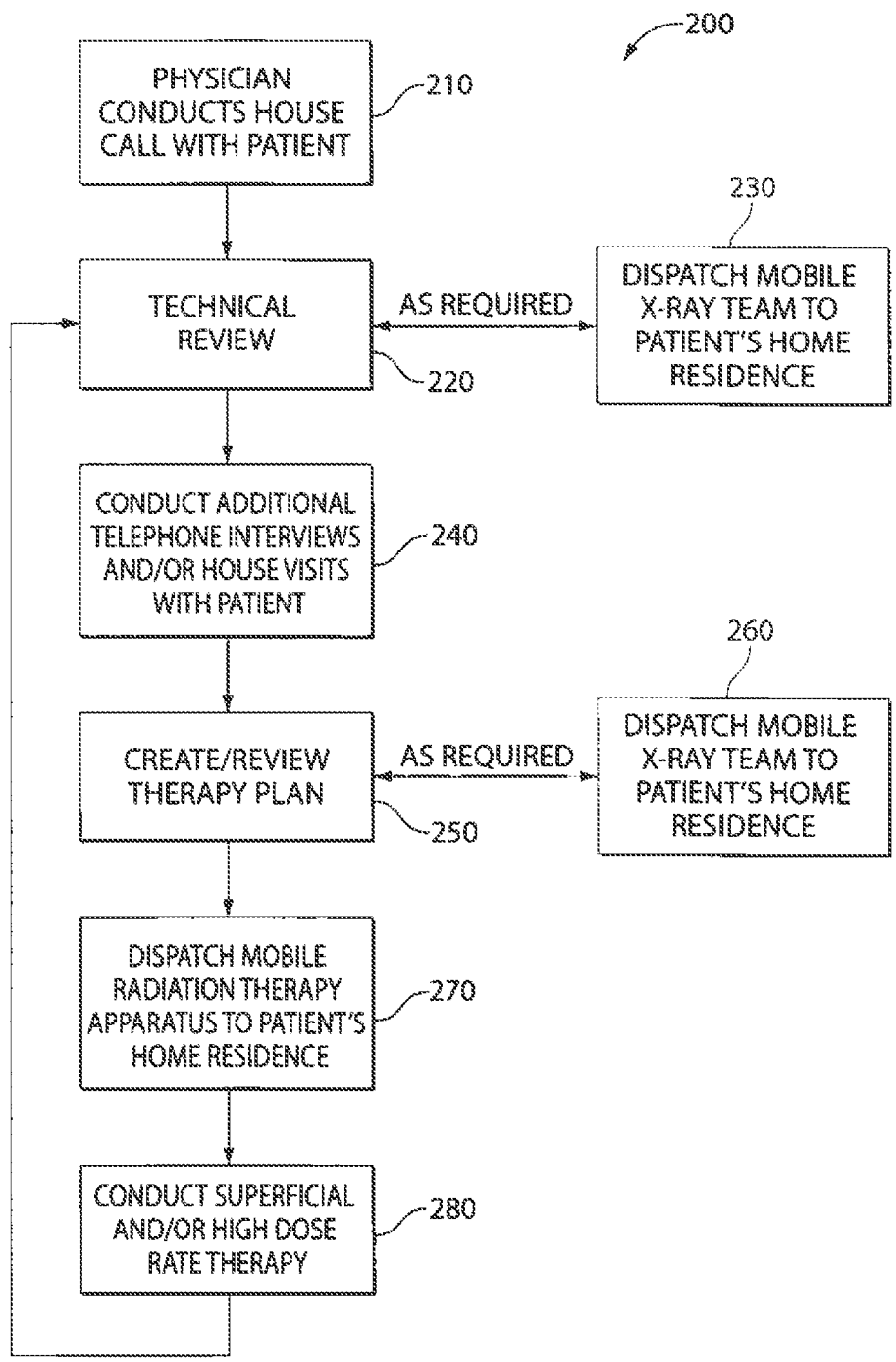
FIG. 6 a process flow chart for providing mobile radiation therapy.

In operation, referring to FIG. 6, with further reference to FIGS. 2-5, a process 200 for providing mobile radiation therapy using the MRTA 10 includes the stages shown. The process 200, however, is exemplary only and not limiting. The process 200 may be altered, e.g., by having stages added, removed, or rearranged.

At stage 210, a physician, physician extender, or other representative makes a house call and reviews any relevant diagnostic studies in order to assess a patient. The house call includes general patient consulting, actual physical tumor measurements, assessments of normal adjacent dose limiting structures, treatment planning, and obtaining digital photos, as well as portable x-rays where necessary. Also, all consent forms are obtained at the initial consult, including HIPPA forms and any other forms and insurance information. This initial house call can be more than just information gathering. For example, it creates a personal bond between the patient and physician and helps increase patient commitment to the program and thereby increase chances for successful treatment.

At stage 220, the physician, physician extender, or other representative, takes the information back to a centralized headquarters area for technical review. A technical review involves a technical department (e.g. therapists, dosimetrists, nurses, and physicists), or similar staff to complete a technical analysis. The technical department processes the information as needed to plan a therapy. For example, additional x-rays may be required, in which case a MRTA 10 will be dispatched to obtain them at stage 230. The technical department also accesses existing x-rays available via hard films (CT scans, PET scans, MRI scans, Bone scans, etc.), or via digital mediums such as memory discs or the internet.

At stage 240, and based on the technical review at stage 220, additional telephone phone contact with the patient, as well as additional visits may be required. This individual treatment helps to ensure that the patient feels a sense of individual commitment as well as confidence in the treatment program. This sense of commitment in turn helps improve compliance with the prescribed therapy. The individual treatment also helps reduce the frustrations associated with stationary cancer centers, such as the long queue time patients must endure while simultaneously being surrounded by sick patients who are often likely to complain and promote a pessimistic outlook.

At stage 250, a radiation therapy plan is created or reviewed by the physician, or physician extender. Additional x-rays will be obtained by dispatching a MRTA 10 to the patient's home residence at stage 260.

At stage 270, the MRTA 10 is dispatched to the patient's home residence or other appropriate location (i.e. treatment location). A simulation is performed on site (i.e., the patient's home residence) by the physician, or physician extender, in the mobile radiation therapy unit. This simulation is expedited by the measurements completed in earlier stages, and by the technical analysis completed at stage 220. This reduces patient waiting time when the actual simulation is preformed most of the background work has been reviewed, calculated and approved. The reduced time is especially appreciated by the patients, who are often in discomfort from this or other diagnosis. The dispatched MRTA 10 is equipped with the appropriate radiation source 28 to complete the therapy plan indicated at stage 250 (e.g., low dose rate and high dose rate sources). The MRTA 10 vehicle is sufficiently compact in size to travel to the patient's residence to begin therapy in the patient's parking lot or residential driveway (e.g., the MRTA 10 compartment is approximately 28' long by 8' wide).

At stage 280, the patient under goes radiation treatment in accordance with the prescribed therapy plan as indicated at stage 250.

Figure 7:
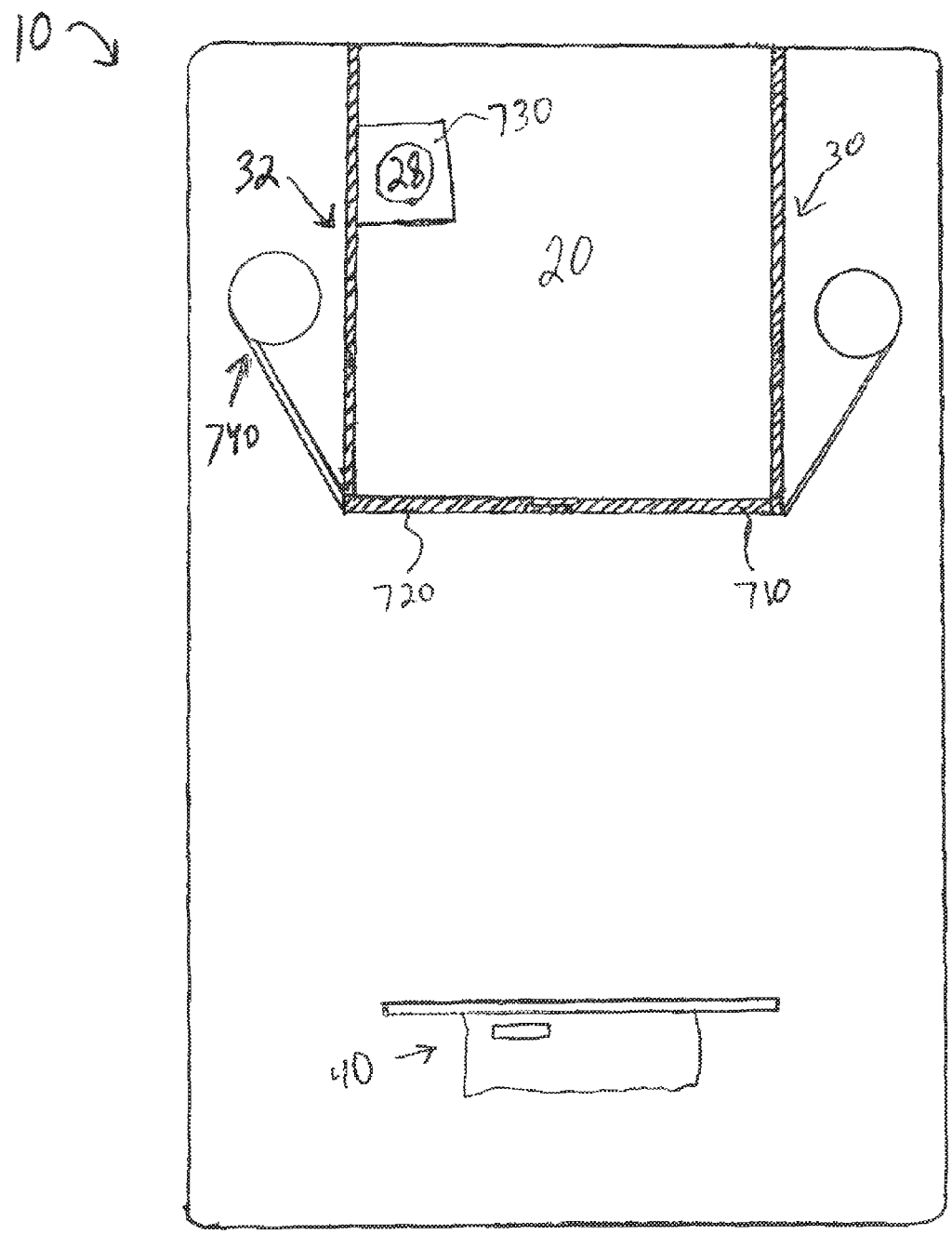
FIG. 7 a partial interior view of another embodiment of a mobile radiation therapy apparatus, wherein non-planar doors are illustrated in the closed position.
Figure 8:
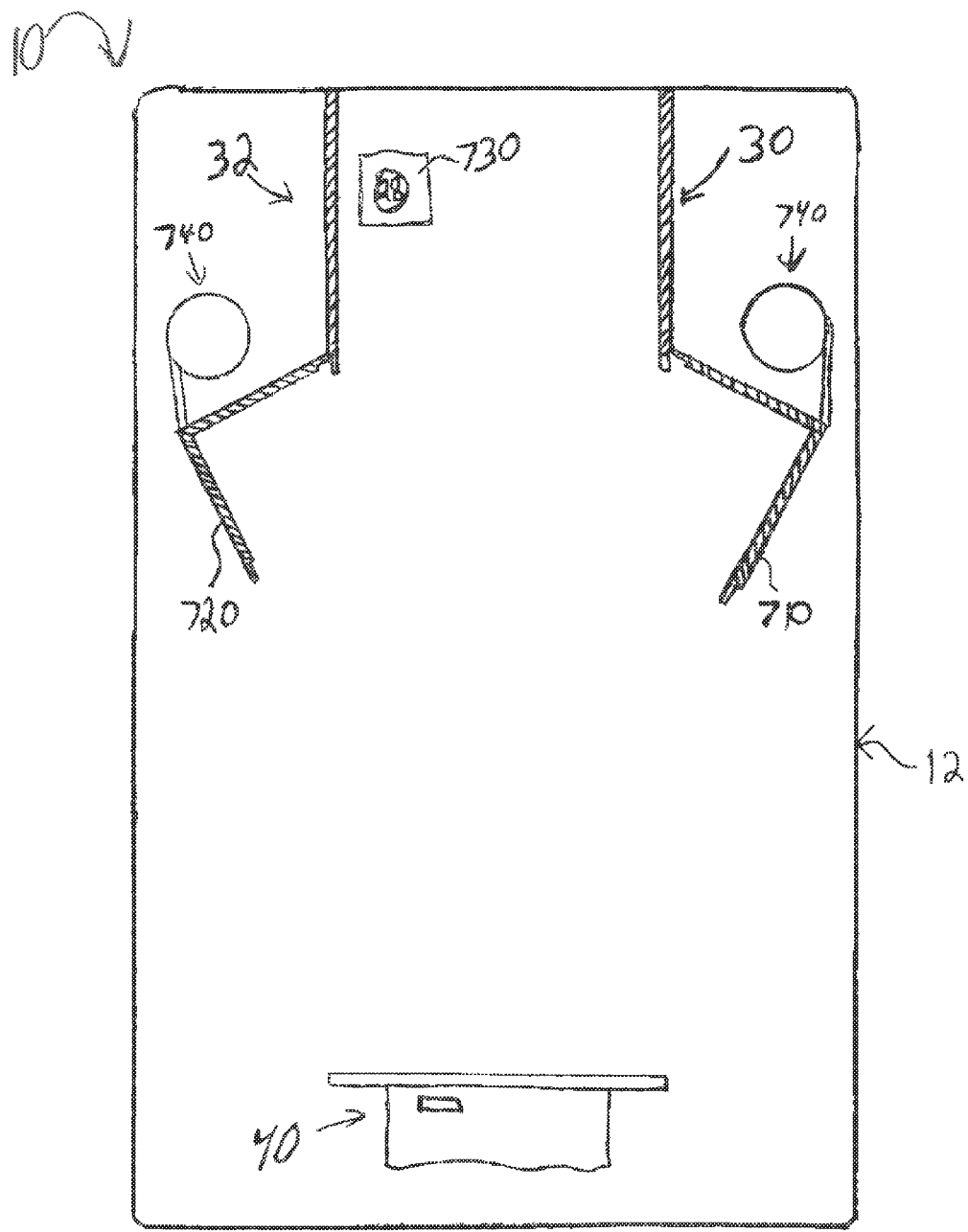
FIG. 8 a partial interior view of another embodiment of a mobile radiation therapy apparatus, wherein non-planar doors are illustrated in the open position.
Figure 9:
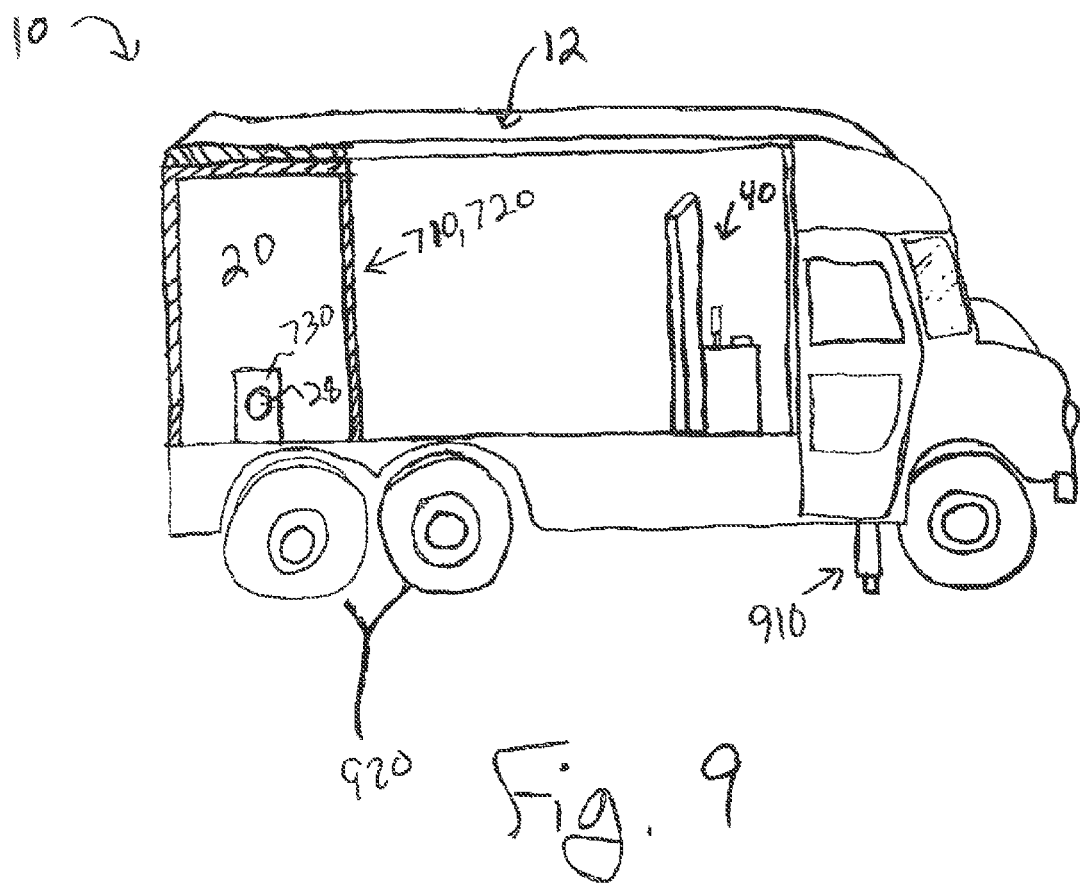
FIG. 9 is a profile side view of another embodiment of a mobile radiation therapy apparatus illustrating a multi axle vehicle with a leveling structure.

Referring now to FIG. 7 and FIG. 8, in a further embodiment of the present invention the patient area radiation bulkheads 30, 32 includes at least one, but preferably a pair of non-planar doors 710, 720 moveably coupled thereto. The non-planar doors are structured to open and close and to thereby define an interior of the compartment 20 when closed. Looking specifically to the preferred non-planar doors 710, 720, they are configured such that when closed, the interior of the compartment extends beyond a leading edge of at least one, but preferably both of the bulkheads 30, 32, thereby providing a larger and more accommodating interior of the compartment 20. Specifically, unlike a flat door that would simply span the preferably parallel bulkheads 30, 32 and would thus confine the interior to the length of the bulkheads 30, 32, by including at least one, but preferably the two non-planar doors 710 and 720, the interior dimension of the compartment 20 extends outward and can more effectively and comfortably accommodate a preferably adjustable patient table 26, a patient chair or bench, or a patient in a wheelchair or on a gurney. Further, the increased space also improves the patient experience as they are not as tightly confined as may otherwise be the case.

Although only a single non-planar door could be used and can span the bulkheads 30,32 while still providing the added space, and/or other non-planar shapes including rounded configuration doors could be used, in the illustrated embodiment the doors 710, 720 include an L-shaped configuration. As shown, each L-shaped door 710, 720 is hingedly secured at one edge to a corresponding bulkhead 30, 32, with the opposite edges of the non-planar doors 710, 720 structured to engage one another in a preferably slightly overlapping and/or interlocking configuration, thereby effectively containing the radiation. Indeed, the non-planar doors 710, 720 are preferably at least partially formed from a radiation shielding material so as to effectively contain the radiation emitted form the radiation source 28 disposed in the compartment 20.

It is also recognized that the L-shaped configuration of the doors 710, 720 maximizes the space in the interior of the compartment 20, but also allows for the most clearance into the compartment 20 when they are open. In particular, in order to facilitate open access to the compartment, and regardless of the specific non-planar shape employed, the non-planar doors 710, 720 are preferably configured to open beyond a width of the patient treatment compartment 20. In this manner the doors will not obstruct access to the compartment by the patient, and in situations wherein a bulky wheelchair or gurney is disposed in the compartment, will allow a practitioner some access and mobility into the compartment before or after a procedure. In order to facilitate this maximized opening of the non-planar doors, the width of the cabin within which the compartment is defined is preferably greater than a width of the compartment 20 as defined by the bulkheads 30, 32.

As noted, the patient treatment compartment 20 is preferably defined within a cabin 12, the cabin 12 being associated with and moveable with a vehicle. Specifically, the cabin 12 is preferably part of the vehicle such that it is a single contained unit as illustrated, however, it is recognized that a trailer type configuration structured to be mounted on or towed by a vehicle may also be provided. Regardless, the cabin 12 is configured to be mobile and effectively contain the remainder of the MRTA 10. Furthermore, the cabin is preferably sufficiently elongate so as to allow some spacing between the compartment 20 and the operator station and control computer 40. In particular, in a preferred embodiment the operator will preferably be at least 10 feet from the radiation source 28 and/or even more preferred, from a confronting perimeter the compartment 20 defined by the closed non-planar doors 710, 720 of the compartment 20. In this way, when combined with the shielding provided by the non-planar doors, the operator will not experience potentially hazardous exposure to the radiation during a treatment.

Although not required, in order to help accommodate an elongate cabin 12 and/or more weight, and thereby maximize the spacing from the operator to the radiation source 28, but also preferably to help accommodate a larger compartment 20 which can accommodate wheelchairs and gurneys, the vehicle associated with the cabin 12 is preferably a multi axle vehicle, including preferably a vehicle with at least two rear axles 920. In this manner a more elongate cabin can be provided, but also, the increase capacity of such a multi axle vehicle increases the weight capacity of the vehicle. Accordingly, the shielding provided in the bulkheads 30, 32 and the non-planar doors 710, 720 can be thicker, but also the larger non-planar doors 710, 720 to define a larger interior of the compartment 20 can be utilized. Further, the bulkheads 30, 32 as well as the non-planer doors 710, 720 can extend completely to the floor of the cabin 12 and to a sufficient height to allow for easier access to the compartment 20 and a more comfortable experience to the user. Also, it is noted that by extending the bulkheads 30, 32 and the doors 710, 720 to the floor of the compartment 20, but more importantly a distance below the radiation source, radiation disbursement beneath the cabin, if any, is reduced, and more of the radiation is contained within the compartment 20 by the bulkheads 30, 32 and the doors 710, 720.

As indicated, the non-planar doors 710, 720 are preferably substantially large and shielded, but regardless, they are substantially heavy. Therefore, in order to facilitate movement of the doors 710, 720 between their open and closed configurations, at least one, but preferably two motors 740 are provided. The motors 740, which can include any type of motor, including but not limited to a piston configuration a gear configuration, or any other type of automated, powered configuration, are powered by the vehicle or a separate battery or power source and are structured to at least be actuated by an operator outside of the compartment 20. In alternative embodiments, the non-planar doors 710, 720 may be adapted to enable the doors to be filled (and emptied following usage) with a liquid following door closure to help shield radioactivity. Thus, such embodiments allow for a lighter material, such as, but not limited to acrylic, to be used.

In order to further facilitate the closing and opening of the non-planar doors 710, 720, under the force of the one or more motors 740, the present MRTA 10 also preferably includes at least one, but preferably a pair of spaced levelers 910. The leveler 910, which may be manual and/or powered, and can include a piston or mechanical structure, is structured to adjust and level the orientation of the cabin 12. Specifically, in many cases the ground upon which the vehicle, and therefore the cabin 12 is positioned is often not level, and indeed at roadsides more often slopes downward for drainage. In view of the preferred size and shielding, and therefore weight of the non-planar doors 710, 720, even a small tilt in the level of the cabin 12 can significantly increase the force required to close the doors 710, 720, often to possible point of not allowing them to be closed. As such, a leveler 910 is provided so as to allow an operator to manually level the cabin 12 when needed, and thereby to allow for more effective and efficient movement of the doors 710, 720 as needed.

Recognizing that a plurality of different radiation sources 28 may be employed within the present invention, and also recognizing that a particular radiation source 28 may be used at multiple treatment locations and/or may need to be stored when not in used, the MRTA 10 may further comprise a mount 730 disposed at least partially within the patient treatment compartment 20. The mount 730 preferably includes a bracketed frame, mounted either directly within the main area of the compartment 20 and/or within a niche or alcove associated therewith, wherein it may removably and selectively receive the desired radiation source 28.

As would be understood by those skilled in the art, the bulkheads, walls and radiation shielding used within the MRTA 10 comprise various degrees of lead and steel which may vary in thickness based on the location of the radiation source 28 and/or based on the amount of radiation that must be prevented from spilling outside of the patient treatment compartment 20 to provide a safe environment to a user. Therefore, in some embodiments, the weight of the MRTA 10, particularly the weight of the MRTA 10 in the area of the patient treatment compartment 20 where more extensive amounts of lead are utilized, may require the use of the previously described multiple axles on the vehicle.

Embodiments of the MRTA 10 include extendable pop-out walls (e.g., hinged or cantilevered) located on the side of the vehicle. The extendable pop-out walls are configured to keep pedestrian traffic at a safe distance from the patient compartment 20. Also, a shielded drape can be placed over or on top of the applicator to decrease the shielding requirements in the walls 18a-e and the bulkheads 30, 32. The MRTA 10 is also configured with interlocks to secure the radiation source 28 when a potentially unsafe condition exists. Such security enhancements include security cameras with proximity sensors configured to provide information to the operator station 40. The vehicle control cabin 12 can include infra-red sensors configured to detect an occupant and trigger an interlock. Visual and audible alarms can be interfaced with the safety interlocks (i.e., proximity, door, radiation detection).

Another embodiment includes an MRTA 10 configured to provide chemotherapy including exam tables, seats, and intravenous apparatus along with standard monitoring equipment and personnel required during chemotherapy. Other embodiments of the MRTA 10 are configured to allow mobile surgery simultaneously with intra-operative radiation therapy, or post-operative radiation therapy and chemotherapy in a mobile setting.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. To be transported by a vehicle, a mobile radiation therapy apparatus comprising:
   a portable enclosure structured to be at least temporarily secured to the vehicle and to move with the vehicle;
   a patient treatment compartment defined in said portable enclosure;

a radiation source disposed on said portable enclosure and structured to emit radiation into said patient treatment compartment;

at least one patient area radiation bulkhead, said patient area radiation bulkhead structured to at least partially define a perimeter of said patient treatment compartment and to at least partially enclose said radiation source; and said patient area radiation bulkhead comprising a plurality of wall panels, each of said wall panels made of glass and including a liquid fillable interior space structured to receive a radiation impeding liquid therein when radiation is to be emitted from said radiation source and to be emptied of liquid when said portable enclosure is to move with the vehicle, thereby reducing the weight to be moved by the vehicle.

2. A mobile radiation therapy apparatus as recited in claim 1 wherein said portable enclosure comprises a vehicle cabin with driving controls for the vehicle.

3. A mobile radiation therapy apparatus as recited in claim 1 wherein said plurality of panels further include at least one opening structured to facilitate the introduction and removal of said liquid relative to said liquid fillable interior space.

4. A mobile radiation therapy apparatus as recited in claim 1 wherein said glass is leaded glass.

5. A mobile radiation therapy apparatus as recited in claim 1 wherein said radiation source is configured to emit radiation for high-dose radiation therapy.

6. A mobile radiation therapy apparatus as recited in claim 1 further comprising a control computer operatively connected to the radiation source and configured to control the radiation emitted by the radiation source.

7. A mobile radiation therapy apparatus as recited in claim 1, wherein said liquid is water.

8. A mobile radiation therapy apparatus as recited in claim 1, further comprising an x-ray imaging system.

9. A method for providing mobile radiation therapy, comprising: dispatching a mobile radiation therapy apparatus of claim 1 to any one of a plurality of treatment locations on a periodic basis and administering radiation therapy to a patient in need thereof.

10. A method as recited in claim 9 further comprising dispatching a mobile x-ray team on a periodic basis as part of a mobile radiation plan.

11. A method as recited in claim 9 wherein the administering radiation therapy includes high-dose radiation therapy.

12. A mobile radiation treatment apparatus comprising:
a radiation source configured to emit radiation;
a patient treatment table disposed in proximity to the radiation source;
an operator control station;
an operator shield assembly disposed between the operator control station and the radiation source, the operator shield assembly comprising a plurality of panels, each of which includes a substantially enclosed liquid fillable interior space;
said liquid fillable interior space structured to receive a quantity of liquid structured to cooperate with said panels to impede the passage of radiation through said panels and reduce a user located at said operator control station's exposure to radiation emitted from said radiation source;
a patient table shield disposed around the patient treatment table and configured to impede the passage of said radiation emitted from said radiation source therethrough, said patient table shield including a panels having a liquid fillable interior space structured to receive liquid therein;

said patient treatment table being configured to be selectively moved between a first unshielded position relative to said patient table shield and a second shielded position relative to said patient table shield; and said panels structured to permit the evacuation of said liquid from said liquid fillable interior spaces so as to reduce an overall weight of said operator shield assembly and said patient table shield and thereby facilitate the movement of the apparatus.

13. A mobile radiation treatment apparatus as recited in claim 12 wherein said plurality of panels comprise glass.

14. A mobile radiation treatment apparatus as recited in claim 13 wherein said glass is leaded glass.

15. A mobile radiation treatment apparatus as recited in claim 12 apparatus wherein said liquid is water.

16. To be transported by a vehicle, a mobile radiation therapy apparatus comprising:
a portable enclosure structured to be at least temporarily secured to the vehicle and to move with the vehicle;
a patient treatment compartment defined in said portable enclosure;
a radiation source disposed on said portable enclosure and structured to emit radiation into said patient treatment compartment;
at least one movable radiation bulkhead structured to open and close so as to provide access into and out of an interior of said patient treatment compartment and to at least partially enclose said radiation source when in a closed orientation; and
said moveable radiation bulkhead comprising a wall panel, said wall panel including a liquid fillable interior space structured to receive a radiation impeding liquid therein when radiation is to be emitted from said radiation source and to be selectively emptied of liquid when said radiation source is not in use, thereby reducing a weight of said moveable bulkhead during opening and closing and during movement of the vehicle, and
said wall panel and said liquid are at least partially transparent so as to permit light to enter said patient treatment compartment.

17. To be transported by a vehicle, a mobile radiation therapy apparatus comprising:
a portable enclosure structured to be at least temporarily secured to the vehicle and to move with the vehicle;
a patient treatment compartment defined in said portable enclosure;
a radiation source disposed on said portable enclosure and structured to emit radiation into said patient treatment compartment;
at least one patient area radiation bulkhead, said patient area radiation bulkhead structured to at least partially define a perimeter of said patient treatment compartment and to at least partially enclose said radiation source;
said patient area radiation bulkhead comprising a plurality of wall panels, each of said wall panels including a liquid fillable interior space structured to receive a radiation impeding liquid therein when radiation is to be emitted from said radiation source and to be emptied of liquid when said portable enclosure is to move with the vehicle, thereby reducing the weight to be moved by the vehicle, and
a portable radiation shield comprising glass and configured to be removed from the mobile radiation therapy apparatus and disposed in proximity to the radiation source.

18. A mobile radiation therapy apparatus as recited in claim 17 wherein said glass is leaded glass to further impede the passage of radiation therethrough.

\* \* \* \* \*